(12) United States Patent
Lee et al.

(10) Patent No.: US 8,945,937 B2
(45) Date of Patent: Feb. 3, 2015

(54) APPARATUS AND METHOD FOR ANALYZING GRAPHENE AND GRAPHENE BOUNDARY

(71) Applicant: Samsung Electronics Co., Ltd., Suwon-si (KR)

(72) Inventors: Young-hee Lee, Suwon-si (KR); Gang-hee Han, Suwon-si (KR); Dinh Loc Duong, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 13/904,526

(22) Filed: May 29, 2013

(65) Prior Publication Data

US 2013/0344611 A1 Dec. 26, 2013

(30) Foreign Application Priority Data

Jun. 20, 2012 (KR) .................... 10-2012-0066320

(51) Int. Cl.
*G01N 21/17* (2006.01)
*C01B 31/04* (2006.01)
*G01B 11/24* (2006.01)

(52) U.S. Cl.
CPC ............ *G01N 21/17* (2013.01); *C01B 31/0484* (2013.01); *C01B 31/0438* (2013.01); *G01B 11/24* (2013.01)
USPC ............... 436/145; 436/80; 436/84; 436/164; 422/82.05; 423/415.1; 428/457

(58) Field of Classification Search
USPC ................ 436/73, 75, 80, 84, 145, 164, 174; 422/82.05; 423/415.1; 428/457
See application file for complete search history.

(56) References Cited

FOREIGN PATENT DOCUMENTS

| JP | 2011-114299 A | 6/2011 |
|---|---|---|
| JP | 5142278 B2 | 2/2013 |
| KR | 10-1089921 B1 | 12/2011 |

OTHER PUBLICATIONS

Duong et al. Nature, vol. 490, Oct. 3, 2012 (online), pp. 235-240.*
Ly et al. Advanced Functional Materials, vol. 23, Apr. 19, 2013 (online), pp. 5183-5189.*
Li, X. et al. "Large-Area Synthesis of High-Quality and Uniform Graphene Films on Copper Foils". Science, vol. 324, p. 1312-1314; Jun. 2009.
Ni, Z. et al. "Graphene Thickness Determination Using Reflection and Contrast Spectroscopy". Nano Letters, vol. 7, No. 9, p. 2758-2763; Jul. 2007.
Ajayan, P. et al. "Graphene: Pushing the boundaries". Nature Materials, vol. 10, p. 415-417; Jun. 2011.
K.D. Kihm et al., "Microscopic Images of Graphene Layers of Different Thicknesses", Journal of Heat Transfer, Aug. 2011, vol. 133.
Pinshane Y. Huang et al., "Grains and grain boundaries in single-layer graphene atomic patchwork quilts", Nature, Jan. 20, 2011, vol. 469, pp. 389-393.

(Continued)

*Primary Examiner* — Maureen Wallenhorst (57) ABSTRACT

A method of analyzing graphene includes providing a first graphene structure including graphene having grains and grain boundaries, and a support portion for supporting the graphene, generating a second graphene structure by oxidizing the first graphene structure, and detecting a shape of the graphene.

23 Claims, 7 Drawing Sheets

(56) References Cited

OTHER PUBLICATIONS

Qingkai Yu et al., "Control and characterization of individual grains and grain boundaries in graphene grown by chemical vapour deposition", Nature: Materials, Jun. 2011, vol. 10, pp. 443-449.

Dae Woo Kim et al., "Direct visualization of large-area graphene domains and boundaries by optical birefringency", Nature: Nanotechnology, Jan. 2012, vol. 7, pp. 29-34.

* cited by examiner

APPARATUS AND METHOD FOR ANALYZING GRAPHENE AND GRAPHENE BOUNDARY

CROSS-REFERENCE TO RELATED APPLICATIONS

This application claims the benefit of Korean Patent Application No. 10-2012-0066320, filed on Jun. 20, 2012, in the Korean Intellectual Property Office, the disclosure of which is incorporated herein in its entirety by reference.

BACKGROUND

1. Field

Example embodiments relate to an apparatus and method for analyzing properties of grains and grain boundaries of synthesized graphene.

2. Description of the Related Art

At present, as carbon-based materials, fullerenes, carbon nanotubes, diamonds, graphite and/or graphene are being researched in various fields.

Among those materials, carbon nanotubes have been spotlighted since the 1990s, but recently, graphene having a sheet structure has attracted attention. Graphene is a thin-film material in which carbon atoms are two-dimensionally arranged, and inside graphene, electric charges work as zero-effective mass particles, such that graphene is known as having relatively high electric conductivity, high heat conductivity, and high elasticity.

Therefore, properties of graphene have been studied, and research has also been conducted to utilize graphene in various fields. In particular, graphene may be used to implement a transparent electrode which can be used in interconnections of a circuit board, which is essentially installed in electric and electronic devices, or a display device.

To use graphene in industrial fields, there is a need for a technique for synthesizing large-area graphene and a technique for analyzing properties of synthesized graphene.

Graphene synthesized to have a relatively large area is mainly formed of polycrystals, and in this case, properties of graphene may be recognized by analyzing the shapes of grains and grain boundaries. That is, as the size of the grain increases, electric and thermal properties of the synthesized graphene are improved.

As techniques for analyzing grains and grain boundaries of graphene, there are an atomic force microscope (AFM), a scanning electron microscope (SEM), a transmission electron microscopy (TEM), and/or dispersive Raman. However, these analyzing methods may cause inconvenience of manufacturing a sample for analysis and/or may analyze only a local portion of several μm or below.

SUMMARY

Example embodiments provide an apparatus and method for analyzing properties of graphene through analysis of grains and grain boundaries of large-area graphene. Additional aspects will be set forth in part in the description which follows and, in part, will be apparent from the description, or may be learned by practice of example embodiments.

According to example embodiments, a method of analyzing graphene includes providing a first graphene structure including graphene having grains and grain boundaries, and a support portion for supporting the graphene, generating a second graphene structure by oxidizing the first graphene structure, and detecting a shape of the graphene.

The support portion may be made of an oxidizable material, such that the support portion may be made of metal, e.g., at least one metal selected from a group consisting of aluminum (Al), iron (Fe), cobalt (Co), nickel (Ni), copper (Cu), and palladium (Pd).

The support portion may be made of multiple layers. That is, the support portion may include a first support portion contacting the graphene, the first support portion made of metal, and a second support portion supporting the first support portion.

The second graphene structure may be generated by disposing the first graphene structure in an environment including water vapor ($H_2O$) and oxygen (0), and irradiating ultraviolet (UV) rays to the first graphene structure. The method may further include removing moisture after irradiating the UV rays.

A humidity of the environment including the water vapor ($H_2O$) may be about 20% to about 100%. The shape of the graphene may be detected using an optical microscope. The second graphene structure may be generated by oxidizing the first graphene structure including forming an oxide in a part of the support portion abutting the grain boundaries, the oxide having a width larger than a width of the grain boundaries of the graphene.

According to example embodiments, an apparatus of analyzing a graphene structure includes an oxidization unit configured to receive the graphene structure including graphene and a support portion for supporting the graphene, the graphene including grains and grain boundaries, and form oxides by oxidizing parts of the support portion corresponding to the grain boundaries of the graphene, and a graphene shape detection unit configured to detect a shape of the graphene.

The apparatus may further include an analysis unit configured to analyze properties of the graphene from the shape of the graphene.

The oxidization unit may include a humidity adjustment unit configured to supply water vapor and an ultraviolet (UV) light source unit configured to irradiate UV rays to form an oxidizer from the water vapor. The oxidization unit may further include a drying unit configured to remove moisture on a surface of the graphene structure.

The graphene shape detection unit may include an optical microscope for detecting shapes of the grains and the grain boundaries of the graphene. A width of the oxides is larger than a width of the grain boundaries. According to example embodiments, a graphene structure includes graphene including grains and grain boundaries, a support portion supporting the graphene, and an oxide in a part of the support portion abutting the grain boundaries.

A width of the oxide may be larger than a width of the grain boundaries. The support portion may be made of metal, e.g., copper (Cu). The support portion may be formed of multiple layers. For example, the support portion may include a first support portion contacting the graphene and made of copper (Cu) and a second support portion supporting the first support portion. The oxide may include copper hydroxide ($Cu(OH)_2$).

BRIEF DESCRIPTION OF THE DRAWINGS

These and/or other aspects will become apparent and more readily appreciated from the following description of the embodiments, taken in conjunction with the accompanying drawings of which.

DETAILED DESCRIPTION

Hereinafter, a method and apparatus for analyzing graphene according to example embodiments will be described with reference to the accompanying drawings. In the drawings, like reference numerals will refer to like components, and the thickness or size of each layer is exaggerated for convenience in description and clarity.

The present disclosure is not limited to disclosed embodiments and may be implemented in different various forms, and the embodiments are merely provided to teach the category of the present disclosure to those of ordinary skill in the art and the present disclosure is defined by the category of claims of the present disclosure.

The terms used herein are for illustrative purposes of the present disclosure only and should not be construed to limit the meaning or the scope of the present disclosure. As used in this specification, a singular form may, unless definitely indicating a particular case in terms of the context, include a plural form. Also, the expressions "comprise" and/or "comprising" used in this specification neither define the mentioned components, steps, operations, and/or elements, nor exclude the presence or addition of one or more other different components, steps, operations, and/or elements of these, or addition of these. As used herein, terms such as "first," "second," etc., are used to describe various components, but the components should not be defined by the terms. The terms are used to distinguish one component from another component.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments are not to be construed as limited to the particular shapes of regions illustrated herein but are to include deviations in shapes that result, for example, from manufacturing. For example, an implanted region illustrated as a rectangle may have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, is to be interpreted as having a meaning that is consistent with their meaning in the context of the relevant art and will not be interpreted in an idealized or overly formal sense unless expressly so defined herein.

Figure 1A:
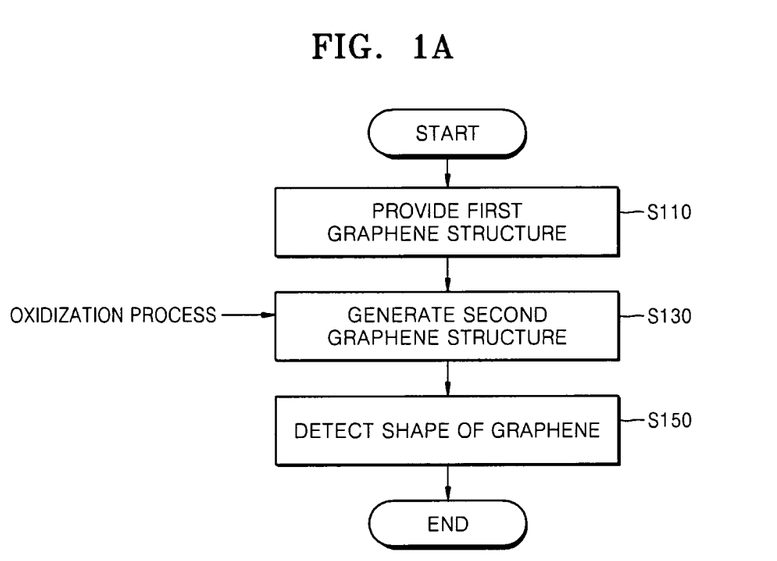
FIG. 1A is a flowchart illustrating a method of analyzing graphene according to example embodiments.

FIG. 1A is a flowchart illustrating a method of analyzing graphene according to example embodiments. The method of analyzing graphene according to example embodiments shown in FIG. 1A includes providing a first graphene structure (S110), generating a second graphene structure by an oxidization process with respect to the first graphene structure (S130), and detecting a shape of graphene (S150).

Graphene is formed in the form of a two-dimensional (2D) flat sheet through covalent bonding between a plurality of carbon atoms, and the carbon atoms connected by covalent bonding form a six-member ring as a basic repetition unit, but a five-member ring and/or a seven-member ring may be further included. Thus, graphene forms a single layer of covalent-bonded carbon atoms (generally, $sp^2$ bond). Graphene may have various structures, and these structures may vary according to a content of a five-member ring and/or a seven-member ring which can be included in graphene.

The method of manufacturing a large-area graphene may be classified into several types: a micro-mechanical method; a SiC crystal thermal decomposition method; and/or a chemical vapor deposition (CVD) method.

In the micro-mechanical method, a sheet of tape (e.g., Scotch tape) may be attached to a graphite sample, and the tape may be stripped off to obtain graphene, removed from the graphite sample, on the surface of the tape.

In the SiC crystal thermal decomposition method, a SiC single crystal may be heated to disintegrate SiC on the surface, thus removing Si. The remaining carbon (C) forms graphene. A graphene synthesizing process using a CVD method may be performed as described below.

A silicon wafer having a silicon oxide ($SiO_2$) layer is provided. A metallic catalyst (e.g., nickel (Ni), copper (Cu), aluminum (Al), or iron (Fe)) may be deposited on the provided silicon oxide ($SiO_2$) layer by using a sputtering device and/or an electron-beam evaporator, thus forming a metallic catalyst layer.

The silicon wafer where the metallic catalyst layer is formed and gas containing carbon ($CH_4$, $C_2H_2$, $C_2H_4$, or CO) are put into a reaction system for thermal-chemical vapor deposition or inductive coupled plasma chemical vapor deposition (ICP-CVD) and are heated to allow carbon to be absorbed in the metallic catalyst layer. Thereafter, rapid cooling is performed to separate carbon from the metallic catalyst layer and crystallize the carbon, such that graphene grows.

When graphene is synthesized using the CVD method, a single plate may be used and a foil made of metal may be used as the single plate. In example embodiments, a metallic plate serves as a metallic catalyst layer. For example, the metallic plate may be a copper foil having a thickness of about 70 μm.

Figure 1B:
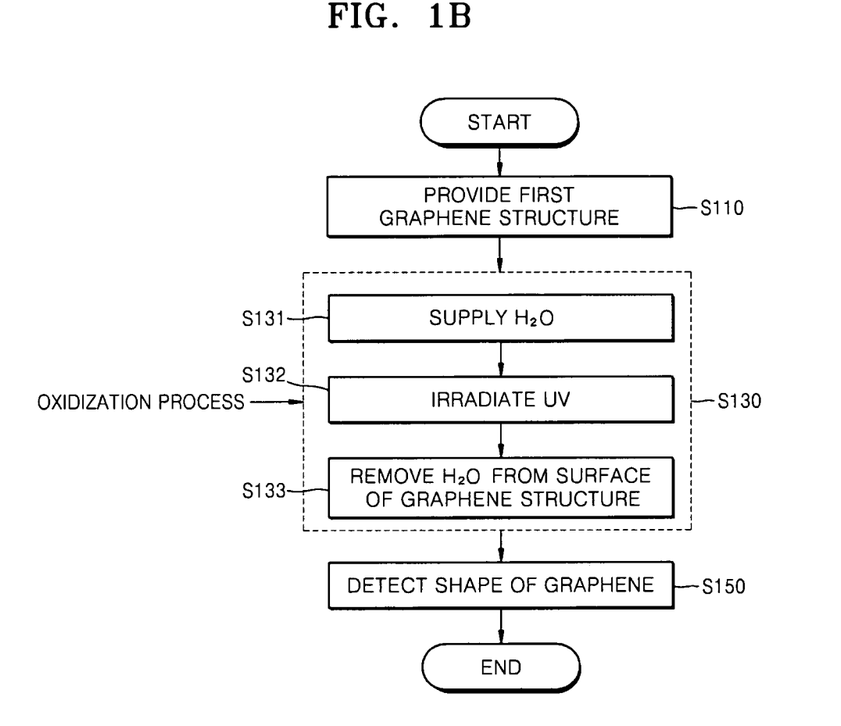
FIG. 1B is a flowchart illustrating a method of analyzing graphene, which includes example embodiments of an oxidization process shown in FIG. 1A.

In the method of analyzing graphene shown in FIGS. 1A and 1B, providing the first graphene structure (S110) is not limited to any one of the aforementioned graphene manufacturing methods, and the graphene structure may be provided using various methods. After graphene is synthesized, graphene structures obtained by transferring the synthesized graphene to other plates or films may be provided for various purposes.

Figure 2A:
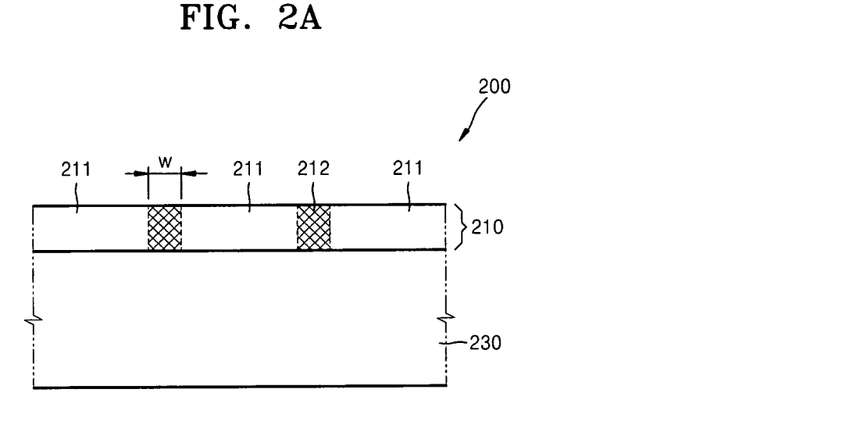
FIGS. 2A and 2B show a side shape of a graphene structure which can be used in example embodiments.
Figure 2B:
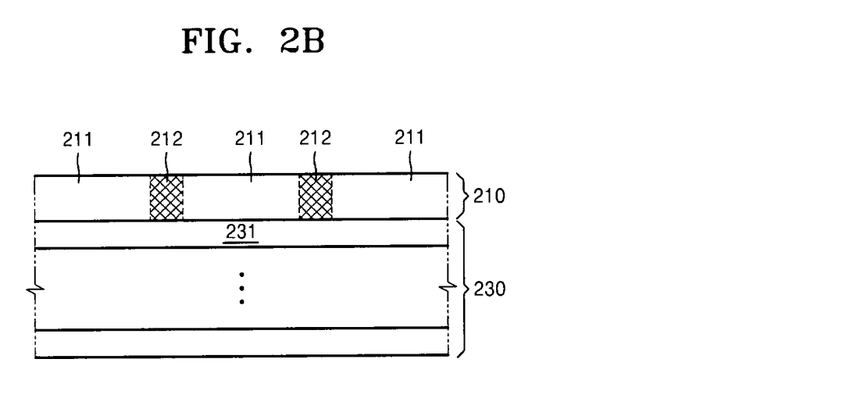

FIGS. 2A and 2B show a side shape of the graphene structure 200 which can be used in example embodiments. Referring to FIGS. 2A and 2B, the first graphene structure 200 includes graphene 210 and a support portion 230 supporting the graphene 210. The support portion 230 may be formed of a single layer or multiple layers.

The support portion 230 may be formed with a plate or/and a metallic catalyst layer where necessary for synthesizing the graphene 210. When the graphene 210 is transferred, the plate or/and the metallic catalyst layer supporting the graphene 210 correspond to the support portion 230.

The graphene 210 may include a region of grains 211 in which carbon atoms are regularly arranged and are continuously covalent-bonded, and a region of grain boundaries 212 which is a region between grains. In the region of the grain boundaries 212, covalent bonding between the carbon atoms is broken or other impurities are included.

When the support portion 230 is formed of a single layer, the support portion 230 may be any material which can be oxidized. Thus, the support portion 230 may be formed of various metals, e.g., aluminum (Al), iron (Fe), cobalt (Co), nickel (Ni), and/or copper (Cu), or may be in the form of various alloys including them. The support portion 230 may also be a semiconductor.

When the support portion 230 is formed of multiple layers, a first support portion 231 corresponds to a layer in which the graphene 210 is disposed and which directly supports the graphene 210. In the present disclosure, the first support portion 231 is formed of an oxidizable material. Thus, the first support portion 231 may be formed of metals, e.g., aluminum (Al), iron (Fe), cobalt (Co), nickel (Ni), and/or copper (Cu), or may be in the form of various alloys including them. The first support portion 231 may also be a semiconductor.

Figure 3:
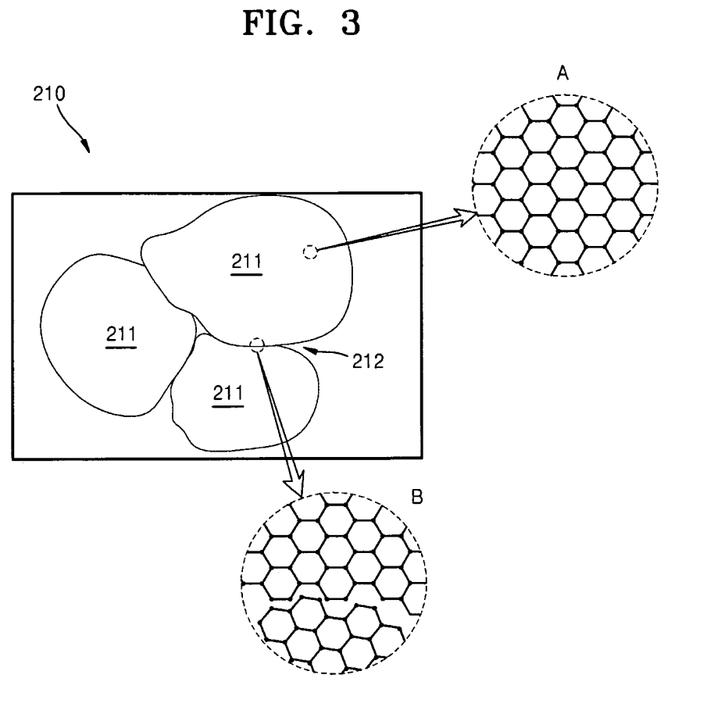
FIG. 3 shows a surface shape of graphene synthesized with polycrystals.

FIG. 3 shows a surface shape of the graphene 210 synthesized with polycrystals. In FIG. 3, A is an enlargement of the region of the grains 211 in which carbon is disposed in a hexagonal shape and B is an enlargement of the region of the grain boundaries 212 in which covalent bonding of carbon is broken. Impurities may permeate a portion in which covalent bonding of carbon is broken.

The most notable property of the graphene 210 is that when electrons move in the graphene 210, the electrons flow as if their mass is zero, which means that the electrons may move at a very high speed (at about 1/300 of light speed as Fermi speed). The mobility of electrons in graphene may have a relatively high value of about 20,000 $cm^2/Vs$ to 200,000 $cm^2/Vs$.

Such a property may be improved as the size of the grains 211 of the graphene 210 increases in the polycrystalline graphene 210. That is, as the size of the grains 211 increases, the mobility of the electrons in the graphene 210 increases and the sheet resistance of the graphene 210 decreases. Thus, detection of the size of the grains 211 of the graphene 210 is one way to analyze the property of the graphene 210, and the size of the grains 211 of the graphene 210 may be detected by how the grain boundaries 212 are formed.

A width 'w' of the grain boundaries 212 of the graphene 210 is several nanometers (nm), such that the width cannot be observed by an optical microscope having a resolution of up to several hundreds of nanometers.

Therefore, to analyze the grains 211 and the grain boundaries 212 of the graphene 210, an atomic force microscope (AFM), a scanning electron microscope (SEM), or a transmission electron microscope may be used or a Raman spectroscopic analysis method may be used. However, such an analysis method causes inconvenience of manufacturing a sample for analysis and/or may analyze only a local portion of several μm or below.

Generally, graphene is known as being observable by an optical microscope. That is, whether graphene of one carbon-atom layer is formed may be recognized by the optical microscope. If graphene is synthesized on silicon oxide ($SiO_2$) having a thickness of 300 nm, interference of light may occur due to multiple reflection on the graphene and a silicon oxide layer. Through such observation, existence of a graphene thin film is merely checked, and the shapes of grains or grain boundaries of the graphene may not be observed.

In example, the shapes of the grain boundaries 212 of the graphene 210 may be observed by a general optical microscope. To this end, by deforming the first graphene structure 200, a sample which is observable with an optical microscope needs to be manufactured, and the sample may be manufactured through generating the second graphene structure (S130) as shown in FIG. 1A.

Generating the second graphene structure (S130) deforms the first graphene structure 200 into the second graphene structure by oxidizing parts of the support portion 230 of the first graphene structure 200, which support the grain boundaries 212 of the graphene 210. Through this process, an oxide may be formed in the portion which supports the grain boundaries 212. A width of the oxide may be several hundreds of nanometers to several micros, e.g., 500 nm to 600 nm, such that the formed oxide may be observable with an optical microscope.

Generating the second graphene structure (S130) may include oxidizing the support portion 230 of the first graphene structure 200, and this process may be performed in various ways which are not particularly limited. Generating the second graphene structure (S130) may be performed variously according to a material of the support portion 230.

FIG. 1B is a flowchart illustrating a method of analyzing graphene, which includes generating the second graphene structure (S130) as shown in FIG. 1A.

Referring to FIG. 1B, generating the second graphene structure (S130) may include placing the first graphene structure 200 in an environment in which water vapor ($H_2O$) is formed (S131) and irradiating ultraviolet (UV) rays to the first graphene structure 200 (S132). In example embodiments, a reaction mechanism may be expressed as below.

Once UV rays are irradiated to oxygen ($O_2$), ozone ($O_3$) is formed, and if UV rays are irradiated in a state where ozone ($O_3$) and water vapor ($H_2O$) exist, an OH-radical is formed. The formed OH-radical is a main oxidizer. That is, the OH-radical passes through the grain boundaries 212 of the graphene 210, thus oxidizing the support portion 230.

The humidity of an environment where the water vapor is formed may be 20% to 100%, for example, 25% to 70%. By irradiating UV rays to the first graphene structure 200 (S130), a time during which the UV rays are irradiated may vary according to the humidity. For example, for a lower humidity, the UV rays may be irradiated for a longer time, and for a higher humidity, the UV rays may be irradiated for a shorter time.

Generating the second graphene structure (S130) may further include removing moisture or $H_2O$ from the surface of the graphene structure (S133). In particular, when generating the second graphene structure (S130) in a higher humidity environment, removing moisture or $H_2O$ from the surface of the graphene structure (S133) may be desirable.

FIGS. 4A through 4D are diagrams showing a process in which some materials which form the first graphene structure 200 are reformed to form the second graphene structure according to the generation of the second graphene structure (S130) as shown in FIG. 1B.

Figure 4A:
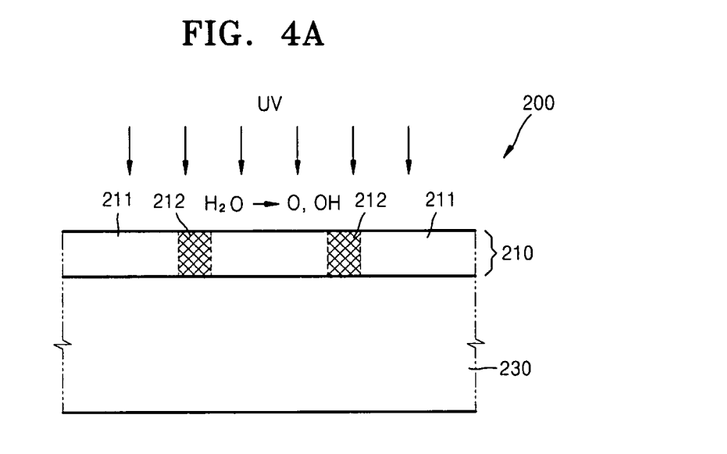
FIGS. 4A through 4D are diagrams showing a process in which some of materials which form a first graphene structure are reformed to form a second graphene structure as shown in FIG. 1B.

FIG. 4A illustrates where the first graphene structure 200 is placed in an environment where the water vapor $H_2O$ is formed, and the UV rays are irradiated onto the first graphene structure 200. At this time, the OH-radical is generated.

Figure 4B:
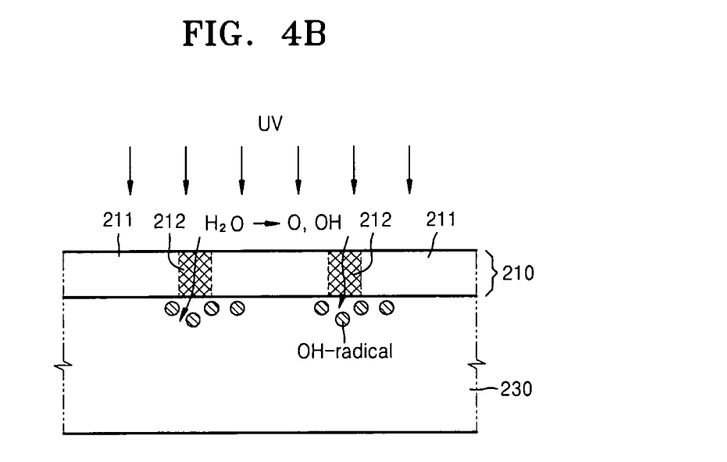

FIG. 4B shows a state where the generated OH-radical passes through the grain boundaries 212 of the graphene 210 and moves to the support portion 230. The grain boundaries 212 of the graphene 210 have a relatively weak bonding force between carbon atoms, such that the OH-radical may pass through the grain boundaries 212.

Figure 4C:
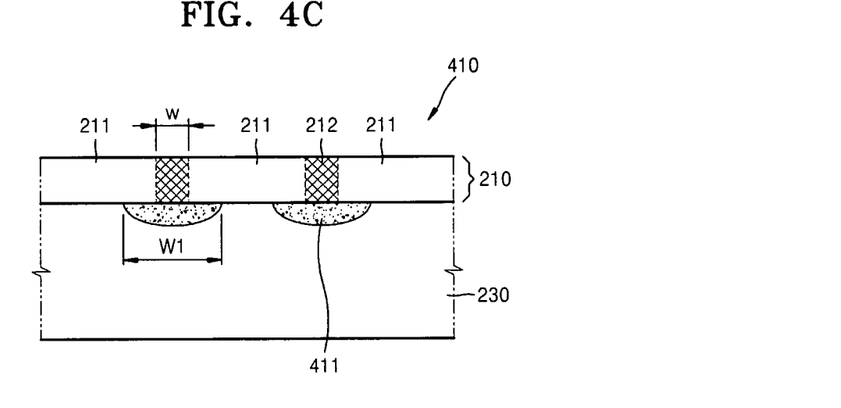
Figure 4D:
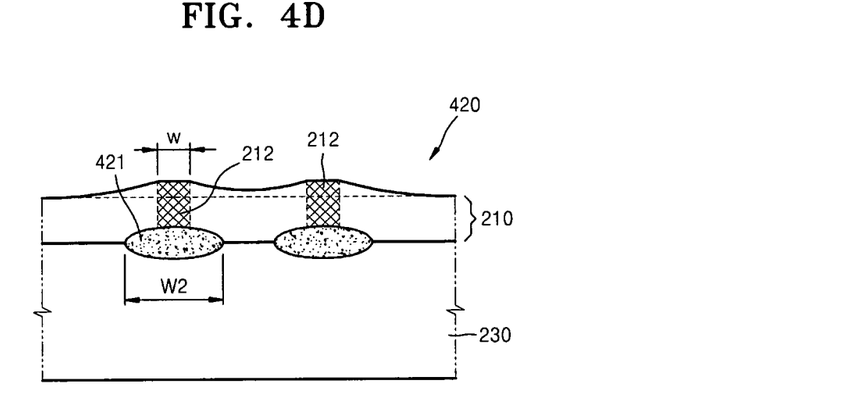

FIGS. 4C and 4D schematically show second graphene structures 410 and 420 which are generated through oxidization of parts of the support portion 230 by the OH-radical.

Once the OH-radical permeates through the grain boundaries 212, the OH-radical oxidizes the support portion 230. The OH-radical makes an oxidation reaction around the parts of the support portion 230 corresponding to the grain boundaries 212. That is, if parts of the support portion 230, which are deformed by oxidization due to the OH-radical, are oxides 411 and 421, then the oxides 411 and 421 are formed around parts corresponding to the grain boundaries 212 of the graphene 210. The oxides 411 and 421 and the support portion 230 have different properties, and the oxides 411 and 421 and the support portion 230 may be optically distinguished based on a difference in refractive index therebetween.

As shown in FIG. 4D, if the OH-radical oxidizes the support portion 230, a volume of the oxidized part may expand. In example embodiments, the part corresponding to the grain boundaries 212 of the graphene 210 is lifted, such that the grains 211 near the grain boundaries 212 may also be lifted. Thus, the grains 211 and the grain boundaries 212 may be distinguished by a difference in height between the grains 211 and the grain boundaries 212 as well as a difference in refractive index between the oxide 421 and the support portion 230.

In the second graphene structures 410 and 420 shown in FIGS. 4C and 4D, widths W1 and W2 of the oxides 411 and 421 are much larger than the width w of the grain boundaries 212. For example, the widths W1 and W2 of the oxides 411 and 421 may be larger by 50 times to 100 times than the width w of the grain boundaries 212. If the widths W1 and W2 of the oxides 411 and 421 are larger than a resolution of an optical microscope, for example, 500 nm to 600 nm, then the oxides 411 and 421 may be observable with the optical microscope. Because the oxides 411 and 421 may be observed with the optical microscope, the shape of the grains may be analyzed over the relatively large area as well as a local portion.

The above-described method of generating a second graphene structure (S130) is merely an example, and may be performed by various embodiments. That is, an oxidizer may be an oxygen (O)-radical or other oxidizing radicals, instead of the OH-radical. Generating the second graphene structure (S130) may further include adjusting a temperature.

Even when the oxides 411 and 421 are formed, the position of the grain boundaries 212 is not changed. Thus, the position of the grain boundaries 212 of the graphene 210 may be recognized by observing the oxides 411 and 421, and the shape and size of the grains 211 of the graphene 210 may be detected from the shape of the grain boundaries 212.

As the size of the grains 211 of the graphene 210 increases, the sheet resistance of the graphene 210 decreases. That is, the size of the grains 211 of the graphene 210 and the sheet resistance of the graphene 210 may have an inverse-proportional relationship therebetween as expressed by:

$$\Omega = \Omega_0 [1 + (A/A_c)^{-1}] \quad (1),$$

wherein $\Omega$ indicates a sheet resistance, A indicates an average size of grains, and $\Omega_0$ and $A_c$ indicate constants. By using this equation, the size of grains of graphene is measured, such that the sheet resistance of the graphene may be analyzed.

Figure 5:
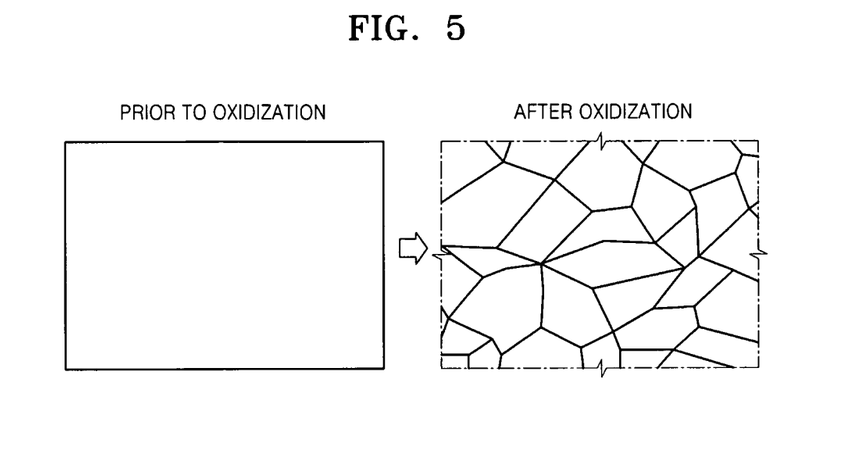
FIG. 5 shows a shape resulting from observation of a surface of graphene synthesized with polycrystals by using an optical microscope.

FIG. 5 shows a shape resulting from observation of the surface of the graphene 210 synthesized with polycrystals using the optical microscope. That is, in FIG. 5, a shape of the first graphene structure 200 observed with an optical microscope prior to generating the second graphene structure (S130) and a shape of the second graphene structures 410 and 420 observed with the optical microscope after generating the second graphene structure (S130) are shown.

Referring to FIG. 5, prior to generating the second graphene structure (S130), the grain boundaries 212 of the first graphene structure 200 cannot be observed with a resolution of a general optical microscope. However, after generating the second graphene structure (S130), the oxides 411 and 421 of the second graphene structures 410 and 420 may be formed in the grain boundaries 212 of the graphene 210, such that the shapes of the grains 211 and the grain boundaries 211 are observable.

Figure 6:
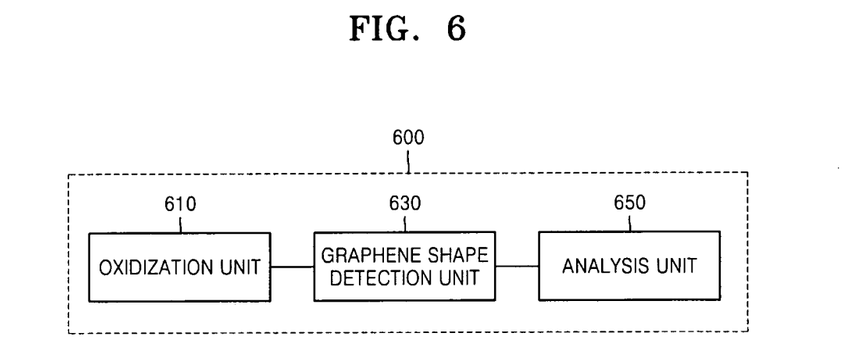
FIG. 6 is a block diagram of an apparatus for analyzing graphene by using a method of analyzing graphene according to example embodiments.

FIG. 6 is a block diagram of an apparatus 600 for analyzing graphene by using a method of analyzing graphene according to example embodiments. To analyze the first graphene structure 200 including the support portion 230 and the graphene 210, which is disposed in at least a side of the support portion 230 and in which the grains 211 and the grain boundaries 212 are formed, the apparatus 600 for analyzing graphene according to example embodiments may include an oxidization unit 610 which forms the oxides 411 and 421 by oxidizing parts of the support portion 230 corresponding to the grain boundaries 212, and a graphene shape detection unit 630.

The apparatus 600 for analyzing graphene by using a method of analyzing graphene according to example embodiments may further include an analysis unit 650 for measuring the size of the grains 212 of the graphene 210 or measuring a sheet resistance of the graphene 210 based on the size of the grains 212.

The oxidization unit 610 may include a humidity adjustment unit for supplying water vapor and an UV light source unit for irradiating UV rays to form an oxidizer which oxidizes the support portion 230 from the water vapor.

The oxidization unit 610 may further include a drying unit for removing moisture formed on the surface of the graphene structure. The oxidization unit 610 may further include a temperature adjustment unit for adjusting the temperature of the graphene structure for an oxidization reaction. As a gas for transporting the water vapor, an argon gas or an oxygen gas may be included.

The above-described method and apparatus for analyzing graphene may be executed by a microprocessor which uses software or a program code coded to execute the method or function. The design, development, and implementation of the code may be obvious to those of ordinary skill in the art based on the description of example embodiments.

According to the above-described method and apparatus for analyzing graphene, a sample for graphene property analysis may be simply manufactured. That is, copper used in synthesis may be used as a support. Moreover, the shape of grains of the graphene may be observable with a simple analysis tool, e.g., the optical microscope, such that the properties of the graphene may be simply analyzed. In addition, the analysis may be performed over the relatively large area as well as a local portion of the graphene. Therefore, the time, cost, and effort for graphene property analysis can be reduced and the method may be used as a monitoring process in manufacturing.

While the method and apparatus for analyzing graphene and the graphene structure for graphene analysis according to example embodiments have been described with reference to the embodiments shown in the drawings to facilitate understanding, they are merely examples and those of ordinary skill in the art will understand that various modifications and equivalent other embodiments may be made from them. Accordingly, the true technical scope of the present disclosure should be defined by the appended claims.

What is claimed is:

1. A method of analyzing graphene, the method comprising:
   providing a first graphene structure including,
      graphene having grains and grain boundaries, and
      a support portion for supporting the graphene;
   generating a second graphene structure by oxidizing the first graphene structure; and
   detecting a shape of the graphene.

2. The method of claim 1, wherein the support portion is made of an oxidizable material.

3. The method of claim 2, wherein the support portion is made of metal.

4. The method of claim 3, wherein the support portion includes at least one of aluminum (Al), iron (Fe), cobalt (Co), nickel (Ni), copper (Cu), and palladium (Pd).

5. The method of claim 1, wherein the support portion comprises:
   a first support portion contacting the graphene, the first support portion made of metal; and
   a second support portion supporting the first support portion.

6. The method of claim 1, wherein the generating a second graphene structure comprises:
   disposing the first graphene structure in an environment including water vapor ($H_2O$) and oxygen (O); and
   irradiating ultraviolet (UV) rays to the first graphene structure.

7. The method of claim 6, further comprising:
   removing moisture after irradiating the UV rays.

8. The method of claim 6, wherein the disposing the first graphene structure includes disposing the first graphene structure in the environment having a humidity of about 20% to about 100%.

9. The method of claim 1, wherein the detecting a shape of the graphene includes using an optical microscope.

10. The method of claim 1, wherein the generating a second graphene structure by oxidizing the first graphene structure includes forming an oxide in a part of the support portion abutting the grain boundaries, the oxide having a width larger than a width of the grain boundaries of the graphene.

11. An apparatus for analyzing a graphene structure comprising:
    an oxidization unit configured to receive the graphene structure including graphene and a support portion for supporting the graphene, the graphene including grains and grain boundaries, and form oxides by oxidizing parts of the support portion corresponding to the grain boundaries of the graphene; and
    a graphene shape detection unit configured to detect a shape of the graphene after the graphene structure has been oxidized by the oxidation unit.

12. The apparatus of claim 11, further comprising:
    an analysis unit configured to analyze properties of the graphene from the shape of the graphene.

13. The apparatus of claim 11, wherein the oxidization unit comprises:
    a humidity adjustment unit configured to supply water vapor; and
    an ultraviolet (UV) light source unit configured to irradiate UV rays to form an oxidizer from the water vapor.

14. The apparatus of claim 13, wherein the oxidization unit further comprises a drying unit configured to remove moisture on a surface of the graphene structure.

15. The apparatus of claim 11, wherein the graphene shape detection unit comprises an optical microscope configured to detect shapes of the grains and the grain boundaries of the graphene.

16. The apparatus of claim 15, wherein a width of the oxides is larger than a width of the grain boundaries.

17. A graphene structure comprising:
    graphene including grains and grain boundaries;
    a support portion supporting the graphene; and
    an oxide in a part of the support portion abutting the grain boundaries.

18. The graphene structure of claim 17, wherein a width of the oxide is larger than a width of the grain boundaries.

19. The graphene structure of claim 17, wherein the support portion is made of metal.

20. The graphene structure of claim 19, wherein the support portion is made of copper (Cu).

21. The graphene structure of claim 20, wherein the oxide includes copper hydroxide ($Cu(OH)_2$).

22. The graphene structure of claim 17, wherein the support portion comprises:
    a first support portion contacting the graphene, the first support portion made of copper (Cu); and
    a second support portion supporting the first support portion.

23. The graphene structure of claim 22, wherein the oxide includes copper hydroxide ($Cu(OH)_2$).

* * * * *